United States Patent
Skranc et al.

(10) Patent No.: US 11,634,401 B2
(45) Date of Patent: *Apr. 25, 2023

(54) PROCESS-SCALE SYNTHESIS OF UROLITHIN A

(71) Applicant: Amazentis SA, Lausanne (CH)

(72) Inventors: Wolfgang Skranc, Vienna (AT); George Yiannikouros, Florence, SC (US); Alexander Trofimov, Florence, SC (US); Zhixing Shan, Albany, NY (US); Christopher Goss, Florence, SC (US)

(73) Assignee: Amazentis SA, Lausanne (CH)

( * ) Notice: Subject to any disclaimer, the term of this patent is extended or adjusted under 35 U.S.C. 154(b) by 10 days.

This patent is subject to a terminal disclaimer.

(21) Appl. No.: 17/141,472

(22) Filed: Jan. 5, 2021

(65) Prior Publication Data

US 2021/0198225 A1    Jul. 1, 2021

Related U.S. Application Data

(63) Continuation of application No. 16/287,347, filed on Feb. 27, 2019, now Pat. No. 10,906,883.

(60) Provisional application No. 62/765,125, filed on Aug. 17, 2018, provisional application No. 62/635,893, filed on Feb. 27, 2018.

(51) Int. Cl.
   *C07D 311/80* (2006.01)
   *B01J 27/055* (2006.01)

(52) U.S. Cl.
   CPC .......... *C07D 311/80* (2013.01); *B01J 27/055* (2013.01)

(58) Field of Classification Search
   CPC .................................................. C07D 311/80
   See application file for complete search history.

(56) References Cited

U.S. PATENT DOCUMENTS

| | | | |
|---|---|---|---|
| 3,957,852 | A | 5/1976 | Fujikawa et al. |
| 5,519,133 | A | 5/1996 | Crews, Jr. et al. |
| 10,906,883 | B2 | 2/2021 | Skranc et al. |
| 2005/0282781 | A1 | 12/2005 | Ghosal |
| 2008/0031862 | A1 | 2/2008 | Ghosal |
| 2012/0270915 | A1 | 10/2012 | Woodward et al. |

FOREIGN PATENT DOCUMENTS

| | | | | |
|---|---|---|---|---|
| EP | | 0122518 A1 | 10/1984 | |
| EP | | 3354645 A1 | 8/2018 | |
| EP | | 3412274 A1 | 12/2018 | |
| WO | WO-2010/020363 A1 | | 2/2010 | |
| WO | WO-2015/100213 A2 | | 7/2015 | |
| WO | WO-2017/135286 A1 | | 8/2017 | |
| WO | WO-2017135286 A1 | * | 8/2017 | .......... A61K 31/352 |
| WO | WO-2019/168972 A1 | | 9/2019 | |

OTHER PUBLICATIONS

WO 2017/135286 A1, Machine English language translation provided from WIPO website. (Year: 2017).*
Berge, Stephen, et al. "Pharmaceutical Salts." Journal of Pharmaceutical Sciences. (Jan. 1977). vol. 66, No. 1, pp. 1-19. (Year: 1977).*
Bell et al., "3-Aminopyrrolidinone farnesyltransferase inhibitors: design of macrocyclic compounds with improved pharmacokinetics and excellent cell potency," Journal of medicinal chemistry, 45(12):2388-2409 (2002).
Bialonska et al., "Urolithins, intestinal microbial metabolites of pomegranate ellagitannins, exhibit potent antioxidant activity in a cell-based assay," Journal of Agricultural and Food Chemistry, 57(21):10181-10186 (2009).
Bringmann et al., "First Atropo-Divergent Total Synthesis of the Antimalarial Korupensamines A and B by the "Lactone Method"," The Journal of organic chemistry, 65(7):2069-2077 (2000).
Cozza et al., "Urolithin as a converging scaffold linking ellagic acid and coumarin analogues: design of potent protein kinase CK2 inhibitors," ChemMedChem, 6(12):2273-2286 (2011).
Extended European Search Report Received for EP Patent application No. 17153423.3, dated Mar. 29, 2017.
Garazd et al., "Modified coumarins. 15. Condensed psoralen derivatives based on substituted dibenzo [b, d] pyran-6-ones," Chemistry of natural compounds, 40(6):535-540 (2004).
Ghosal et al., "Interaction of Shilajit with biogenic free radicals," Indian Journal of Chemistry Section, 34B(7):596-602 (1995).
Gonzalez-Sarrias et al., "The gut microbiota ellagic acid-derived metabolite urolithin A and its sulfate conjugate are substrates for the drug efflux transporter breast cancer resistance protein (ABCG2/BCRP)," Journal of agricultural and food chemistry, 61(18):4352-4359 (2013).
González-Sarrías et al., "Neuroprotective effects of bioavailable polyphenol-derived metabolites against oxidative stress-induced cytotoxicity in human neuroblastoma SH-SY5Y cells," Journal of agricultural and food chemistry, 65(4):752-758 (2016).
Hoarau et al., "A versatile synthesis of poly-and diversely substituted isoindolin-1-ones," Synthesis, 5:655-660 (2000).
International Search Report and Written Opinion for International Application No. PCT/US2019/019817 dated Apr. 23, 2019.
Ito et al., "Identification of urinary and intestinal bacterial metabolites of ellagitannin geraniin in rats," Journal of agricultural and food chemistry, 56(29):393-400 (2007).
Lederer et al., "Synthese de la dihydroxy-4.4' dibenzo-alpha pyrone, pigment des glandes a parfum du castor (castor fiber)," Bulletin De La Societe Chimique De France, 831-834 (1948).
Pandey et al., "Synthesis and biological activities of some new dibenzopyranones and dibenzopyrans: search for potential oestrogen receptor agonists and antagonists," Bioorganic & medicinal chemistry, 12(9):2239-2249 (2004).

(Continued)

*Primary Examiner* — John S Kenyon
(74) *Attorney, Agent, or Firm* — Foley Hoag LLP; Dana M. Gordon; Lawrence P. Tardibono

(57) ABSTRACT

Disclosed are methods for preparing a salt of urolithin A and, in turn, urolithin A. The methods are advantageous for the large-scale preparation of urolithin A or a pharmaceutically acceptable salt thereof.

23 Claims, 2 Drawing Sheets

(56) References Cited

OTHER PUBLICATIONS

Saha et al., "Gut microbiota conversion of dietary ellagic acid into bioactive phytoceutical urolithin A inhibits heme peroxidases," Plos One, 11(6):1-21 (2016).
Scarborough et al., "Substitution in the methyl-4'-nitro-and-4'-acetamido-diphenyl ethers," Journal of the Chemical Society, 52-56 (1934).
Schlosser et al., "1, 2-Didehydro-3-and-4-(trifluoromethoxy) benzene: The "Aryne" Route to 1-and 2-(Trifluoromethoxy) naphthalenes," European Journal of Organic Chemistry, 21:3991-3997 (2001).
Ye et al., "Chiral Cp-hodium (III)-Catalyzed Asymmetric Hydroarylations of 1, 1-isubstituted Alkenes," Angewandte Chemie International Edition, 53(2):507-511 (2014).
Berge et al., "Pharmaceutical Salts," Journal of Pharmaceutical Sciences, 66(1):1-19 (1977).

* cited by examiner

PROCESS-SCALE SYNTHESIS OF UROLITHIN A

RELATED APPLICATIONS

This application is continuation of U.S. patent application Ser. No. 16/287,347, filed Feb. 27, 2019; which claims the benefit of priority to U.S. Provisional Patent Application No. 62/765,125 filed Aug. 17, 2018; and U.S. Provisional Patent Application No. 62/635,893, filed Feb. 27, 2018.

BACKGROUND

In recent years, urolithins have been shown to provide numerous human health benefits. Studies from Ryu et al. showed that urolithin A (UA) improves mitochondrial and muscle functions (Nature Medicine (2016) 22, pages 879-888). The studies further demonstrated that UA activation of mitophagy prevented the accumulation of dysfunctional mitochondria with age and, as a result, extended lifespan.

In light of the therapeutic promise of urolithins, a need exists for a safe, economical, reliable, and scalable synthesis approach to manufacture urolithin A. A reliable source of multi-kilo and multi-ton quantities of urolithin A will allow further clinical and commercial development, with the ultimate goal of exploiting its full therapeutic potential.

SUMMARY OF THE INVENTION

One aspect of the present invention is a method for the preparation of a salt of urolithin A, comprising: combining in an alkaline aqueous solution a copper-containing catalyst, 2-bromo-5-hydroxybenzoic acid, and resorcinol, thereby forming the salt of urolithin A. One aspect of the present invention is a method for the preparation of urolithin A from a salt thereof, comprising protonating a salt of urolithin A to yield urolithin A.

DETAILED DESCRIPTION

Figure 1:
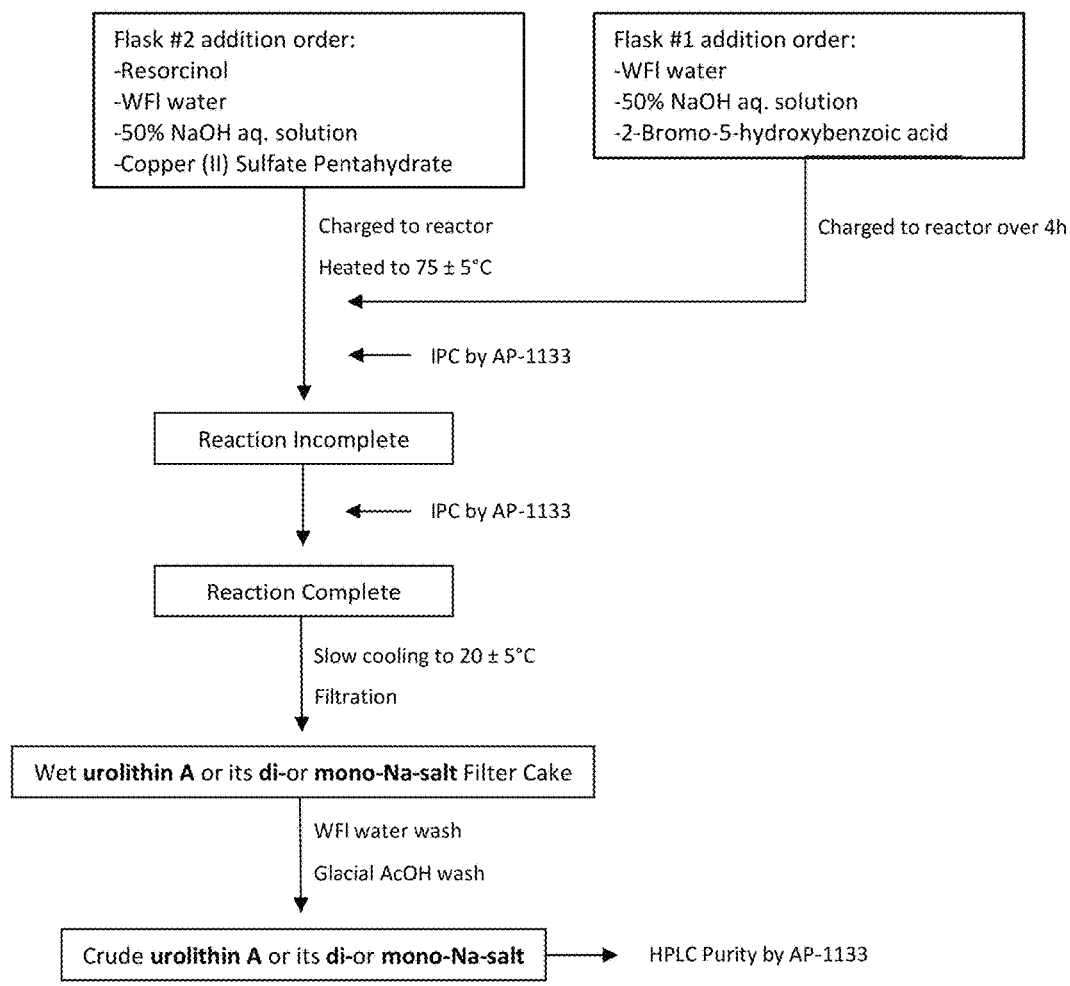
FIG. 1 is a Process Flow Diagram of Step 1 of a GMP synthesis of Urolithin A.
Figure 2:
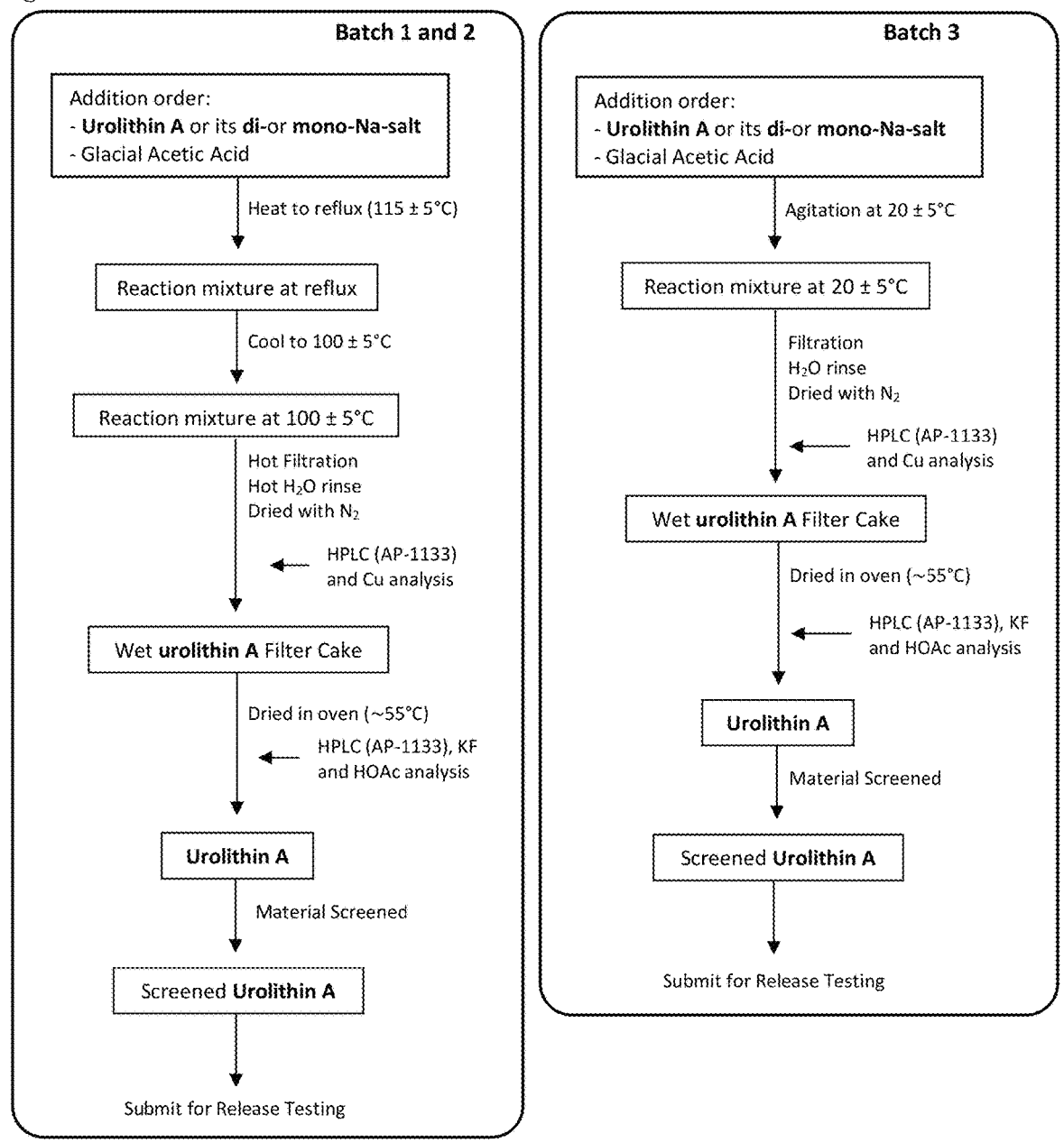
FIG. 2 is a Process Flow Diagram of Step 2 of a GMP synthesis of Urolithin A.

The development of a process-scale synthesis of urolithins required substantial innovation. A useful process-scale synthesis must be efficient, cost-effective, and reproducible. Further, all starting materials and reagents must be reliably available in bulk, or able to be produced on site in a safe and economical fashion. The exacting regulatory standards for low impurity levels and overall safety of the process create additional challenges to development.

Definitions

A number of abbreviations and defined terms are used in this application. Explanations and their definitions appear below.

As used herein, "WFI" refers to water for injection and is water of extra high quality without significant contamination. A sterile version of WFI is used for making solutions that will be given by injection. A non-sterile version may be used in manufacturing, with sterilization occurring later in the production process.

As used herein, compounds which are "commercially available" may be obtained, e.g., from standard commercial sources.

As used herein, "suitable conditions" for carrying out a synthetic step are explicitly provided herein, or may be discerned by reference to publications directed to methods used in synthetic organic chemistry, or are generally known to one of ordinary skill in the art. The reference books and detailed description set forth below that describe the synthesis of intermediates useful in the preparation of compounds of the present invention will also provide suitable conditions for carrying out a synthetic step according to the present invention.

"Stable compound" and "stable structure" are meant to indicate a compound that is sufficiently robust to survive isolation to a useful degree of purity from a reaction mixture, and/or formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted, and that the description includes both substituted aryl radicals and aryl radicals having no substitution.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples below. However, other equivalent separation or isolation procedures can also be used.

Methods of the Invention

One aspect of the invention relates to methods of preparing a salt of urolithin A, comprising: combining in an alkaline aqueous solution a copper-containing catalyst, 2-bromo-5-hydroxybenzoic acid, and resorcinol, thereby forming the salt of urolithin A.

In certain embodiments, the copper-containing catalyst is selected from the group consisting of copper powder, copper-bronze couple, $CuSO_4$ pentahydrate, $CuSO_4$ hydrate, anhydrous $CuSO_4$, $Cu(acac)_2$, $CuCl$, $CuCl_2$, $CuBr$, $CuBr_2$, $CuI$, $Cu_2O$, $CuO$, $CuOTf$, $CuCN$, and mixtures thereof.

In certain embodiments, the copper-containing catalyst is $CuSO_4$ pentahydrate.

In certain embodiments, the amount of the copper-containing catalyst is at least a trace amount but no more than 0.05 molar equivalents relative to the amount of 2-bromo-5-hydroxybenzoic acid.

In certain embodiments, the amount of the copper-containing catalyst is at least a trace amount but no more than 0.02 molar equivalents relative to the amount of 2-bromo-5-hydroxybenzoic acid.

In certain embodiments, the amount of the copper-containing catalyst is at least a trace amount but no more than 0.01 molar equivalents relative to the amount of 2-bromo-5-hydroxybenzoic acid.

In certain embodiments, the amount of the copper-containing catalyst is at least a trace amount but no more than 0.005 molar equivalents relative to the amount of 2-bromo-5-hydroxybenzoic acid.

In certain embodiments, the amount of the copper-containing catalyst is at least a trace amount but no more than 0.001 molar equivalents relative to the amount of 2-bromo-5-hydroxybenzoic acid.

In certain embodiments, the amount of the copper-containing catalyst is at least a trace amount but no more than 0.0005 ($5\times10^{-4}$) molar equivalents relative to the amount of 2-bromo-5-hydroxybenzoic acid.

In certain embodiments, the amount of the copper-containing catalyst is at least a trace amount but no more than 0.0001 ($1\times10^{-4}$) molar equivalents relative to the amount of 2-bromo-5-hydroxybenzoic acid.

In certain embodiments, the alkaline aqueous solution comprises LiOH, NaOH, KOH, CsOH, $Na_2CO_3$, $CaCO_3$, or $Cs_2CO_3$. In certain embodiments, the alkaline aqueous solution comprises LiOH, NaOH, KOH, or CsOH. In certain embodiments, the alkaline aqueous solution comprises NaOH, or KOH. In certain embodiments, the alkaline aqueous solution comprises KOHIn certain embodiments, the alkaline aqueous solution comprises NaOH.

In certain embodiments, the alkaline aqueous solution comprises LiOH, NaOH, KOH, CsOH, $Na_2CO_3$, $CaCO_3$, or $Cs_2CO_3$, and the copper-containing catalyst is $CuSO_4$ pentahydrate.

In certain embodiments, the alkaline aqueous solution comprises LiOH, NaOH, KOH, or CsOH, and the copper-containing catalyst is $CuSO_4$ pentahydrate. In certain embodiments, the alkaline aqueous solution comprises NaOH or KOH, and the copper-containing catalyst is $CuSO_4$ pentahydrate. In certain embodiments, the alkaline aqueous solution comprises KOH, and the copper-containing catalyst is $CuSO_4$ pentahydrate. In certain embodiments, the alkaline aqueous solution comprises NaOH, and the copper-containing catalyst is $CuSO_4$ pentahydrate.

In certain embodiments, the molar ratio of resorcinol to 2-bromo-5-hydroxybenzoic acid is greater than 3:1. In certain embodiments, the molar ratio of resorcinol to 2-bromo-5-hydroxybenzoic acid is greater than 3.5:1. In certain embodiments, the molar ratio of resorcinol to 2-bromo-5-hydroxybenzoic acid is greater than 4:1. In certain embodiments, the molar ratio of resorcinol to 2-bromo-5-hydroxybenzoic acid is about 4:1.

In certain embodiments, the molar ratio of resorcinol to 2-bromo-5-hydroxybenzoic acid is about 3:1 to about 10:1. In certain embodiments, the molar ratio of resorcinol to 2-bromo-5-hydroxybenzoic acid is about 3.5:1 to about 8:1. In certain embodiments, the molar ratio of resorcinol to 2-bromo-5-hydroxybenzoic acid is about 3.5:1 to about 5:1. In certain embodiments, the molar ratio of resorcinol to 2-bromo-5-hydroxybenzoic acid is about 3.5:1 to about 4.5:1. In certain embodiments, the molar ratio of resorcinol to 2-bromo-5-hydroxybenzoic acid is about 3.8:1 to about 4.2:1. In certain embodiments, the molar ratio of resorcinol to 2-bromo-5-hydroxybenzoic acid is about 4.0:1.

In certain embodiments, the alkaline aqueous solution comprises NaOH; and the molar ratio of NaOH to 2-bromo-5-hydroxybenzoic acid is greater than 3:1. In certain embodiments, the alkaline aqueous solution comprises NaOH; and the molar ratio of NaOH to 2-bromo-5-hydroxybenzoic acid is greater than 3.5:1. In certain embodiments, the alkaline aqueous solution comprises NaOH; and the molar ratio of NaOH to 2-bromo-5-hydroxybenzoic acid is greater than 4:1. In certain embodiments, the alkaline aqueous solution comprises NaOH; and the molar ratio of NaOH to 2-bromo-5-hydroxybenzoic acid is about 4:1.

In certain embodiments, the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 2.8:1 to about 5:1. In certain embodiments, the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 3.0:1 to about 4.8:1. In certain embodiments, the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 3.2:1 to about 4.6:1. In certain embodiments, the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 4.2:1 to about 4.6:1. In certain embodiments, the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 4.4:1.

In certain embodiments, the alkaline aqueous solution comprises LiOH, NaOH, KOH, or CsOH; and the molar ratio of LiOH, NaOH, KOH, or CsOH to 2-bromo-5-hydroxybenzoic acid is about 2.8:1 to about 5:1. In certain embodiments, the alkaline aqueous solution comprises LiOH, NaOH, KOH, or CsOH; and the molar ratio of LiOH, NaOH, KOH, or CsOH to 2-bromo-5-hydroxybenzoic acid is about 3.0:1 to about 4.8:1. In certain embodiments, the alkaline aqueous solution comprises LiOH, NaOH, KOH, or CsOH; and the molar ratio of LiOH, NaOH, KOH, or CsOH to 2-bromo-5-hydroxybenzoic acid is about 3.2:1 to about 4.6:1. In certain embodiments, the alkaline aqueous solution comprises LiOH, NaOH, KOH, or CsOH; and the molar ratio of LiOH, NaOH, KOH, or CsOH to 2-bromo-5-hydroxybenzoic acid is about 4.2:1 to about 4.6:1. In certain embodiments, the alkaline aqueous solution comprises LiOH, NaOH, KOH, or CsOH; and the molar ratio of LiOH, NaOH, KOH, or CsOH to 2-bromo-5-hydroxybenzoic acid is about 4.4:1.

In certain embodiments, the alkaline aqueous solution comprises NaOH or KOH; and the molar ratio of NaOH or KOH to 2-bromo-5-hydroxybenzoic acid is about 2.8:1 to about 5:1. In certain embodiments, the alkaline aqueous solution comprises NaOH or KOH; and the molar ratio of NaOH or KOH to 2-bromo-5-hydroxybenzoic acid is about 3.0:1 to about 4.8:1. In certain embodiments, the alkaline aqueous solution comprises NaOH or KOH; and the molar ratio of NaOH or KOH to 2-bromo-5-hydroxybenzoic acid is about 4.2:1 to about 4.6:1. In certain embodiments, the alkaline aqueous solution comprises NaOH or KOH; and the molar ratio of NaOH or KOH to 2-bromo-5-hydroxybenzoic acid is about 4.4:1.

In certain embodiments, the alkaline aqueous solution comprises KOH; and the molar ratio of KOH to 2-bromo-5-hydroxybenzoic acid is about 3.2:1 to about 4.6:1. In certain embodiments, the alkaline aqueous solution comprises KOH; and the molar ratio of KOH to 2-bromo-5-hydroxybenzoic acid is about 2.8:1 to about 5:1. In certain embodiments, the alkaline aqueous solution comprises KOH; and the molar ratio of KOH to 2-bromo-5-hydroxybenzoic acid is about 3.0:1 to about 4.8:1. In certain embodiments, the alkaline aqueous solution comprises KOH; and the molar ratio of KOH to 2-bromo-5-hydroxybenzoic acid is about 3.2:1 to about 4.6:1. In certain embodiments, the alkaline aqueous solution comprises KOH; and the molar ratio of KOH to 2-bromo-5-hydroxybenzoic acid is about 4.2:1 to about 4.6:1. In certain embodiments, the alkaline aqueous solution comprises KOH; and the molar ratio of KOH to 2-bromo-5-hydroxybenzoic acid is about 4.4:1.

In certain embodiments, the alkaline aqueous solution comprises NaOH; and the molar ratio of NaOH to 2-bromo-5-hydroxybenzoic acid is about 2.8:1 to about 5:1. In certain embodiments, the alkaline aqueous solution comprises NaOH; and the molar ratio of NaOH to 2-bromo-5-hydroxybenzoic acid is about 3.0:1 to about 4.8:1. In certain embodiments, the alkaline aqueous solution comprises NaOH; and the molar ratio of NaOH to 2-bromo-5-hydroxybenzoic acid is about 3.2:1 to about 4.6:1. In certain embodiments, the alkaline aqueous solution comprises NaOH; and the molar ratio of NaOH to 2-bromo-5-hydroxybenzoic acid is about 4.2:1 to about 4.6:1. In certain embodiments, the alkaline aqueous solution comprises NaOH; and the molar ratio of NaOH to 2-bromo-5-hydroxybenzoic acid is about 4.4:1.

In certain embodiments, the alkaline aqueous solution comprises NaOH; and the molar ratio of NaOH to 2-bromo-5-hydroxybenzoic acid is about 3:1 to about 10:1. In certain embodiments, the alkaline aqueous solution comprises NaOH; and the molar ratio of NaOH to 2-bromo-5-hydroxybenzoic acid is about 3.5:1 to about 8:1. In certain embodiments, the alkaline aqueous solution comprises NaOH; and the molar ratio of NaOH to 2-bromo-5-hydroxybenzoic acid is about 3.5:1 to about 5:1. In certain embodiments, the alkaline aqueous solution comprises NaOH; and the molar ratio of NaOH to 2-bromo-5-hydroxybenzoic acid is about 3.5:1 to about 4.5:1. In certain embodiments, the alkaline aqueous solution comprises NaOH; and the molar ratio of NaOH to 2-bromo-5-hydroxybenzoic acid is about 3.8:1 to about 4.2:1.

In certain embodiments, the molar yield of the salt of urolithin A is at least about 40% relative to the amount of 2-bromo-5-hydroxybenzoic acid. In certain embodiments, the molar yield of the salt of urolithin A is at least about 50% relative to the amount of 2-bromo-5-hydroxybenzoic acid. In certain embodiments, the molar yield of the salt of urolithin A is at least about 60% relative to the amount of 2-bromo-5-hydroxybenzoic acid. In certain embodiments, the molar yield of the salt of urolithin A is at least about 70% relative to the amount of 2-bromo-5-hydroxybenzoic acid. In certain embodiments, the molar yield of the salt of urolithin A is at least about 80% relative to the amount of 2-bromo-5-hydroxybenzoic acid. In certain embodiments, the molar yield of the salt of urolithin A is at least about 90% relative to the amount of 2-bromo-5-hydroxybenzoic acid.

In certain embodiments, the salt of urolithin A is urolithin A monosodium salt.

In certain embodiments, the salt of urolithin A is urolithin A disodium salt.

In certain embodiments, the salt of urolithin A is isolated in a purity of at least 90%. In certain embodiments, the salt of urolithin A is isolated in a purity of at least 95%. In certain embodiments, the salt of urolithin A is isolated in a purity of at least 97%. In certain embodiments, the salt of urolithin A is isolated in a purity of at least 98%. In certain embodiments, the salt of urolithin A is isolated in a purity of at least 99%. In certain embodiments, the salt of urolithin A is isolated in a purity of at least 99.5%. In certain embodiments, the salt of urolithin A is isolated in a purity of at least 99.8%. In certain embodiments, the salt of urolithin A is isolated in a purity of at least 99.9%.

In certain embodiments, the alkaline aqueous solution is heated at a temperature in the range of about 60° C. to about 90° C. In certain embodiments, the alkaline aqueous solution is heated at a temperature in the range of about 70° C. to about 80° C. In certain embodiments, the alkaline aqueous solution is heated at a temperature of about 60° C. In certain embodiments, the alkaline aqueous solution is heated at a temperature of about 65° C. In certain embodiments, the alkaline aqueous solution is heated at a temperature of about 70° C. In certain embodiments, the alkaline aqueous solution is heated at a temperature of about 75° C. In certain embodiments, the alkaline aqueous solution is heated at a temperature of about 80° C. In certain embodiments, the alkaline aqueous solution is heated at a temperature of about 85° C. In certain embodiments, the alkaline aqueous solution is heated at a temperature of about 90° C.

In certain embodiments, the method further comprises isolating the salt of urolithin A, to give an isolated salt of urolithin A.

In certain embodiments, the salt of urolithin A is isolated by filtration.

In certain embodiments, the isolated salt of urolithin A contains less than about 1 ppm copper.

In certain embodiments, the method further comprises combining a Bronsted acid and the isolated salt of urolithin A, to give a slurry.

In certain embodiments, the Bronsted acid is a carboxylic acid. In certain embodiments, the carboxylic acid is acetic acid. In certain embodiments, the carboxylic acid is glacial acetic acid.

In certain embodiments, the slurry is heated at a temperature in the range of about 100° C. to about 130° C. In certain embodiments, the slurry is heated at a temperature in the range of about 110° C. to about 120° C. In certain embodiments, the slurry is heated at a temperature of about 100° C. In certain embodiments, the slurry is heated at a temperature of about 105° C. In certain embodiments, the slurry is heated at a temperature of about 110° C. In certain embodiments, the slurry is heated at a temperature of about 115° C. In certain embodiments, the slurry is heated at a temperature of about 120° C. In certain embodiments, the slurry is heated at a temperature of about 125° C. In certain embodiments, the slurry is heated at a temperature of about 130° C.

In certain embodiments, the slurry is maintained at a temperature in the range of about 10 C to about 30° C. In certain embodiments, the slurry is maintained at a temperature in the range of about 15° C. to about 25° C. In certain embodiments, the slurry is maintained at a temperature of about 10° C. In certain embodiments, the slurry is maintained at a temperature of about 15° C.

In certain embodiments, the slurry is maintained at a temperature of about 20° C. In certain embodiments, the slurry is maintained at a temperature of about 25° C. In certain embodiments, the slurry is maintained at a temperature of about 30° C.

In certain embodiments, the method further comprises isolating urolithin A from the slurry. In certain embodiments, urolithin A is isolated by filtration.

In certain embodiments, urolithin A is isolated in a purity of at least 90%. In certain embodiments, urolithin A is isolated in a purity of at least 95%. In certain embodiments, urolithin A is isolated in a purity of at least 97%. In certain embodiments, urolithin A is isolated in a purity of at least 98%. In certain embodiments, urolithin A is isolated in a purity of at least 99%. In certain embodiments, urolithin A is isolated in a purity of at least 99.5%. In certain embodiments, urolithin A is isolated in a purity of at least 99.8%. In certain embodiments, urolithin A is isolated in a purity of at least 99.9%.

In certain embodiments, urolithin A contains less than about 25 ppm copper. In certain embodiments, urolithin A contains less than about 10 ppm copper. In certain embodiments, urolithin A contains less than about 5 ppm copper. In certain embodiments, urolithin A contains less than about 2 ppm copper. In certain embodiments, urolithin A contains about 1 ppm copper. In certain embodiments, urolithin A contains less than about 1 ppm copper.

In certain embodiments, a synthetic step in the production of a urolithin is performed in an atmosphere comprising oxygen. In certain embodiments, a synthetic step in the production of a urolithin is performed in an atmosphere comprising a level of oxygen below the atmospheric level of oxygen. In some embodiments, a synthetic step in the production of a urolithin is performed in an oxygen-free atmosphere. In some embodiments, a synthetic step in the production of a urolithin is performed under nitrogen. In some embodiments, a synthetic step in the production of a urolithin is performed under argon.

Production Step 1

Production Step 2

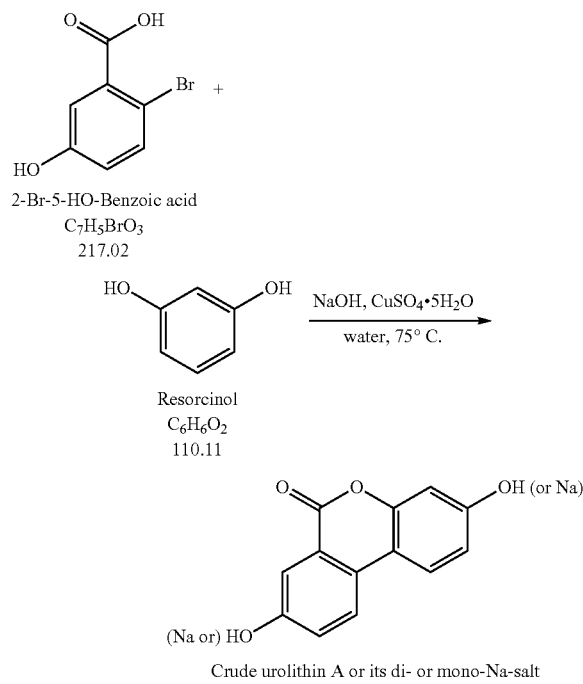

Compositions of the Invention

An aspect of the invention is a composition, comprising copper and urolithin A.

In certain embodiments, the composition comprises <25 ppm copper. In certain embodiments, the composition comprises <10 ppm copper. In certain embodiments, the composition comprises <5 ppm copper. In certain embodiments, the composition comprises <1 ppm copper.

EXEMPLIFICATION

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. The invention now being generally described, it will be more readily understood by reference to the following, which is included merely for purposes of illustration of certain aspects and embodiments of the present invention, and is not intended to limit the invention.

Example 1—Synthesis of Urolithin A

Ullmann-Type Coupling of
2-bromo-5-hydroxybenzoic acid and resorcinol

Described herein is the first step in a short and practical synthesis of urolithins beginning with the commercially available reagents 2-bromo-5-hydroxybenzoic acid and resorcinol.

9

Scheme 1-Reaction Scheme

Production Step 1

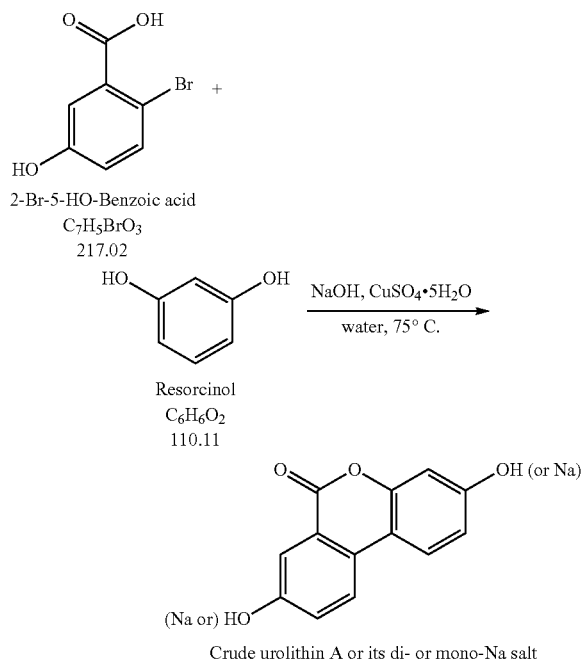

Resorcinol
C$_6$H$_6$O$_2$
110.11

Crude urolithin A or its di- or mono-Na salt

Procedures:
1. To a reactor (Reactor 2), charge Resorcinol (4.00 eq.) and WFI (7 vol.) under N$_2$.
2. Bubble the solution with N$_2$.
3. Charge 50% aq. NaOH-2 (3.30 equiv.) and CuSO$_4$ 5H$_2$O (0.0010 equiv.).
4. Bubble the solution with N$_2$.
5. Polish filter the solution obtained above to a particulate-cleaned and N$_2$-purged reactor (Reactor 3).
6. Wash/rinse the flask/lines with WFI water (3 vol.)
7. Heat the solution in Reactor 3 to 75±5° C.
8. Through a polish filter, slowly charge a pre-prepared solution of 2-bromo-5-hydroxybenzoic acid in Reactor 3 (see the instruction below) via a pump over 4 h while maintaining 75±5° C. Maintain constant addition rate through the course of the addition.
9. Wash/rinse Reactor 3/lines with WFI water (1 vol.)
10. Keep stirring at 75±5° C. for additional 1 h after the addition is complete, and then take the 1$^{st}$ IPC. If the reaction is not complete, then keep stirring at 75° C. until the reaction go to completion.
11. When the reaction is complete, cool the reaction to 20±5° C.
12. Filter the slurry; wash the filter cake with water (5 vol., 4×).
13. Wash the cake with HOAc (5 vol.) and the cake is ready for trituration.

Pre-preparation of the solution of 2-bromo-5-hydroxybenzoic acid required for Step 8:
   a. Charge WFI water (10 vol.) and NaOH (1.10 eq.).
   b. Purge the solution with N$_2$.
   c. Charge 2-bromo-5-hydroxybenzoic acid (1.00 eq.) and agitate until complete dissolution.
   d. Purge the solution with N$_2$.

This reaction is sensitive to oxygen. An N$_2$ atmosphere is beneficial for the reaction.

10

2. Trituration:
Production Step 2. Protonation and Purification

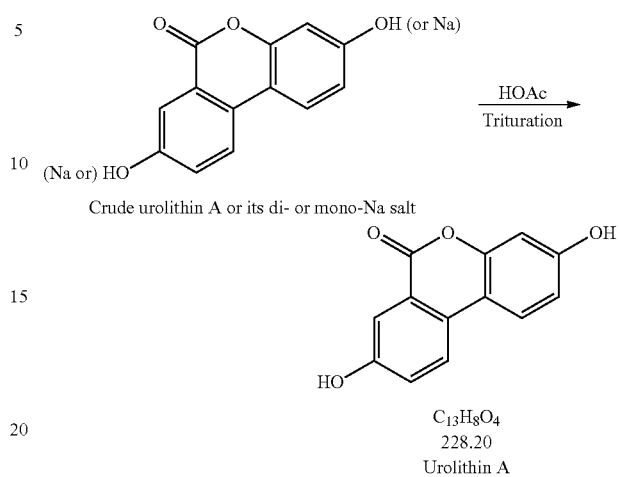

Crude urolithin A or its di- or mono-Na salt

C$_{13}$H$_8$O$_4$
228.20
Urolithin A

Procedures for Trituration at 115±5° C.
1. Charge crude urolithin A or its di- or mono-Na-salt and HOAc (glacial) (20 vol. based on scale of step 1) under N$_2$ to a particulate cleaned reactor with baffle.
2. Heat the slurry to 115±5° C. (target: reflux temp.), and keep agitating the slurry with an aggressive agitation for at least 18 h.
3. Lower the temp. to 100±5° C.
4. Hot filter the slurry while maintaining the slurry temperature at 100±5° C.
5. Wash the cake with hot WFI water (water temp.: 95±5° C.) (5 vol., 4×).
6. HPLC the wet cake.
7. If specs. are met, then go to #8. Otherwise, urolithin A is ready for re-process.
8. Dry the cake until obtaining a consistent mass.

Procedures for Trituration at 20±5° C.
1. Charge crude urolithin A or its di- or mono-Na-salt and HOAc (glacial) (20 vol. based on scale of step 1) under N$_2$ to a particulate cleaned reactor with baffle.
2. Agitate the slurry with an aggressive agitation for at least 18 h.
3. Filter the slurry.
4. Wash the cake with WFI water (5 vol., 4×).
5. HPLC the wet cake.
6. If specs. are met, then go to item #7. Otherwise, urolithin A is ready for re-process.
7. Dry the cake until obtaining a consistent mass.

Example 2—cGMP Production of Urolithin A

Step 1
Batch 1

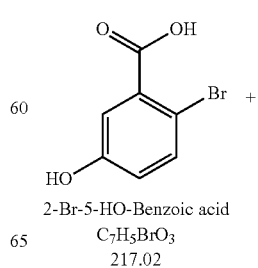

2-Br-5-HO-Benzoic acid
C$_7$H$_5$BrO$_3$
217.02

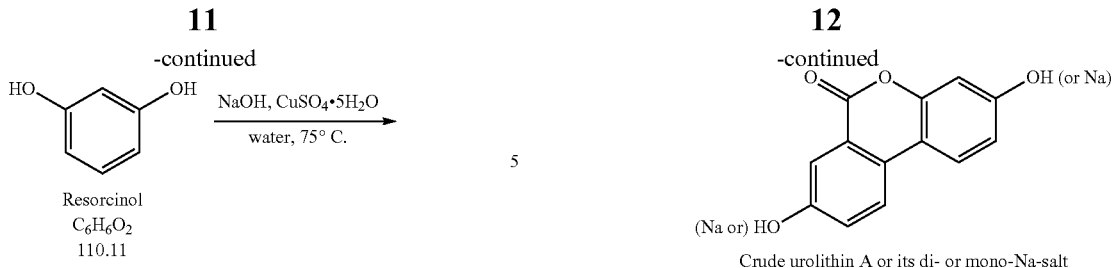

Crude urolithin A or its di- or mono-Na-salt

| Reagents/Materials | MW | Eqs. | Moles | Density | Amt. |
|---|---|---|---|---|---|
| 2-Bromo-5-hydroxybenzoic Acid, ≥99% | 217.02 | 1.00 | 12.2 | — | 2.65 kg |
| 50% (w/w) Sodium Hydroxide, aqueous solution | 40.00 | 4.40 | 53.7 | — | 4.3 kg |
| Resorcinol, ≥99% | 110.11 | 4.00 | 48.8 | — | 5.38 kg |
| Copper (II) Sulfate, Pentahydrate, ≥98% | 249.69 | 0.0010 | 0.0122 | — | 3.0 g |
| Glacial Acetic Acid, ≥99% | 60.05 | 5 vol | — | 1.049 | 13.9 kg |
| Water for Injection Quality (WFI) water | 18.02 | 41 vol | — | 1.00 | 109 kg |

|  |  |
|---:|:---|
|  | To a clean, dry 50-L multi-necked RBF labeled as FLASK #1 (equipped with an agitator motor, agitator fitting, thermowell, thermocouple, condenser, and nitrogen bubbler), |
| 26.5 L | of WFI water was charged. Agitation was started before charging |
| 1.1 kg | of 50% (w/w) Sodium Hydroxide, aqueous solution. Nitrogen was bubbled through the solution for 19 minutes before charging |
| 2.65 kg | of 2-Bromo-5-hydroxybenzoic acid. Nitrogen was bubbled through the solution for 40 minutes. The contents of FLASK #1 were then agitated at 20 ± 5° C. for 1 minute until a complete solution was obtained. FLASK#1 was re-labeled as Step 1.23—FLASK#1—2-Bromo-5-hydroxybenzoic Salt (WFI) aqueous solution, then held under a nitrogen atmosphere until needed. To a clean, dry 50-L multi-necked RBF labeled as FLASK #2 (equipped with an agitator motor, agitator fitting, thermowell, thermocouple, condenser, and nitrogen bubbler), |
| 5.38 kg | of Resorcinol was charged, followed by |
| 18.6 L | of WFI water. Agitation was started. Nitrogen was bubbled through the solution for 16 minutes before charging |
| 3.2 kg | of 50% (w/w) Sodium Hydroxide, aqueous solution. |
| 3.0 g | of Copper (II) Sulfate Pentahydrate was then charged to FLASK #2. Nitrogen was bubbled through the solution for 16 minutes. The contents of FLASK #2 were then agitated at 20 ± 5° C. for 1 minute until a complete solution was obtained. FLASK #2 was re-labeled as Step 1.34—FLASK#2—Resorcinol, (WFI) aqueous solution, then held under a nitrogen atmosphere until needed. To a clean, dry 200-L reactor, the Resorcinol, (WFI) aqueous solution was charged through a polish filter. FLASK #2 was rinsed with |
| 8.0 L | of WFI water, and the rinse was charged to the reactor. The contents were agitated for 32 minutes, while nitrogen was bubbled through the solution, before being heated to 75 ± 5° C. The agitator speed was then set to ~300.79 rpm. While maintaining the temperature at 75 ± 5° C., the 2-bromo-5-hydroxybenzoic Salt (WFI) aqueous solution was charged, through a polish filter, at a rate of ~1.9 kg/15 minutes. FLASK#1 was rinsed with |
| 2.7 L | of WFI water. The rinse was charged to the reactor over 4 minutes while maintaining the temperature at 75 ± 5° C. The contents were then agitated at 75 ± 5° C. for 61 minutes. A representative IPC sample was withdrawn from the reactor and submitted to QC for HPLC analysis. The reaction was deemed incomplete, and was left to stir for additional time before a second IPC sample was submitted to QC. The reaction was then deemed complete. Due to the time sensitivity of the reaction, the IPC results were concluded based on PR&D data. The reactor agitation was then set to ~300 rpm and the contents were slowly cooled to 20 ± 5° C. at a rate of ~5° C./30 minutes. The contents were agitated at 20 ± 5° C. for 1 hour before being filtered through a GMP filter. The reactor was rinsed with |
| 13.3 kg | of WFI water, and the rinse was used to wash the filter cake. The filter cake was then rinsed three more times with |
| 13.3 kg | of WFI water (each wash), followed by |
| 13.9 kg | of Glacial acetic acid. The filter cake was blown dry with nitrogen for 3 hours 27 minutes. A representative sample was then withdrawn from the filter cake and submitted to QC for HPLC purity analysis. ~5.15 kg of wet, crude urolithin A or its di- or mono-Na-salt, were produced, which was carried forward to the next step. |

Batch 2

| Reagents/Materials | MW | Eqs. | Moles | Density | Amt. |
|---|---|---|---|---|---|
| 2-Bromo-5-hydroxybenzoic Acid, ≥99% | 217.02 | 1.00 | 12.2 | — | 2.65 kg |
| 50% (w/w) Sodium Hydroxide, aqueous solution | 40.00 | 4.40 | 53.7 | — | 4.3 kg |
| Resorcinol, ≥99% | 110.11 | 4.00 | 48.8 | — | 5.38 kg |
| Copper (II) Sulfate, Pentahydrate, ≥98% | 249.69 | 0.0010 | 0.0122 | — | 3.0 g |
| Glacial Acetic Acid, ≥99% | 60.05 | 5 vol | — | 1.049 | 13.9 kg |
| Water for Injection Quality (WFI) water | 18.02 | 41 vol | — | 1.00 | 109 kg |

| | |
|---|---|
| | To a clean, dry 50-L multi-necked RBF labeled as FLASK #1 (equipped with an agitator motor, agitator fitting, thermowell, thermocouple, condenser, and nitrogen bubbler), |
| 26.5 L | of WFI water was charged. Agitation was started before charging |
| 1.1 kg | of 50% (w/w) Sodium Hydroxide, aqueous solution. Nitrogen was bubbled through the solution for 18 minutes before charging |
| 2.65 kg | of 2-Bromo-5-hydroxybenzoic acid. Nitrogen was bubbled through the solution for 25 minutes. The contents of FLASK #1 were then agitated at 20 ± 5° C. for 1 minute until a complete solution was obtained. FLASK#1 was re-labeled as Step 1.23—FLASK#1—2-Bromo-5-hydroxybenzoic Salt (WFI) aqueous solution, then held under a nitrogen atmosphere until needed. To a clean, dry 50-L multi-necked RBF labeled as FLASK #2 (equipped with an agitator motor, agitator fitting, thermowell, thermocouple, condenser, and nitrogen bubbler), |
| 5.38 kg | of Resorcinol was charged, followed by |
| 18.6 L | of WFI water. Agitation was started. Nitrogen was bubbled through the solution for 33 minutes before charging |
| 3.2 kg | of 50% (w/w) Sodium Hydroxide, aqueous solution. |
| 3.0 g | of Copper (II) Sulfate Pentahydrate was then charged to FLASK #2. Nitrogen was bubbled through the solution for 15 minutes. The contents of FLASK #2 were then agitated at 20 ± 5° C. for 1 minute until a complete solution was obtained. FLASK #2 was re-labeled as Step 1.34—FLASK#2—Resorcinol, (WFI) aqueous solution, then held under a nitrogen atmosphere until needed. To a clean, dry 200-L reactor, the Resorcinol, (WFI) aqueous solution was charged through a polish filter. FLASK #2 was rinsed with |
| 8.0 L | of WFI water, and the rinse was charged to the reactor. The contents were agitated for 31 minutes, while nitrogen was bubbled through the solution, before being heated to 75 ± 5° C. The agitator speed was then set to ~320 rpm. While maintaining the temperature at 75 ± 5° C., the 2-bromo-5-hydroxybenzoic Salt (WFI) aqueous solution was charged at a rate of ~1.9 kg/15 minutes. FLASK #1 was rinsed with |
| 2.7 L | of WFI water. The rinse was charged to the reactor over 5 minutes while maintaining the temperature at 75 ± 5° C. The contents were then agitated at 75 ± 5° C. for 60 minutes. A representative IPC sample was withdrawn from the reactor and submitted to QC for HPLC analysis. The reaction was deemed incomplete, and was left to stir for additional time before a second IPC sample was submitted to QC. The reaction was then deemed complete. Due to the time sensitivity of the reaction, the IPC results were concluded based on PR&D data. The reactor agitation was then set to ~320 rpm and the contents were slowly cooled to 20 ± 5° C. at a rate of ~5° C./30 minutes. The contents were agitated at 20 ± 5° C. for 37 minutes before being filtered through a Nutsche filter. The reactor was rinsed with |
| 13.3 kg | of WFI water, and the rinse was used to wash the filter cake. The filter cake was then rinsed three more times with |
| 13.3 kg | of WFI water (each wash), followed by |
| 13.9 kg | of Glacial acetic acid. The filter cake was blown dry with nitrogen for 2 hours. A representative sample was then withdrawn from the filter cake and submitted to QC for HPLC purity analysis. ~6.25 kg of wet, crude urolithin A or its di- or mono-Na-salt, were produced, which was carried forward to the next step. |

Batch 3

| Reagents/Materials | MW | Eqs. | Moles | Density | Amt. |
|---|---|---|---|---|---|
| 2-Bromo-5-hydroxybenzoic Acid, ≥99% | 217.02 | 1.00 | 17.2 | — | 3.73 kg |
| 50% (w/w) Sodium Hydroxide, aqueous solution | 40.00 | 4.40 | 75.0 | — | 6.0 kg |
| Resorcinol, ≥99% | 110.11 | 4.00 | 68.7 | — | 7.57 kg |
| Copper (II) Sulfate, Pentahydrate, ≥98% | 249.69 | 0.0010 | 0.0172 | — | 4.3 g |
| Glacial Acetic Acid, ≥99% | 60.05 | 5 vol | — | 1.049 | 19.6 kg |
| Water for Injection Quality (WFI) water | 18.02 | 41 vol | — | 1.00 | 153 kg |

| | |
|---|---|
| | To a clean, dry 50-L multi-necked RBF labeled as FLASK #1 (equipped with an agitator motor, agitator fitting, thermowell, thermocouple, condenser, and nitrogen bubbler), |
| 37.3 L | of WFI water was charged. Agitation was started before charging |
| 1.5 kg | of 50% (w/w) Sodium Hydroxide, aqueous solution. Nitrogen was bubbled through the solution for 48 minutes before charging |
| 3.73 kg | of 2-Bromo-5-hydroxybenzoic acid. Nitrogen was bubbled through the solution or 23 minutes. The contents of FLASK #1 were then agitated at 20 ± 5° C. for 1 minute until a complete solution was obtained. FLASK#1 was re-labeled as Step 1.23—FLASK#1—2-Bromo-5-hydroxybenzoic Salt (WFI) aqueous solution, then held under a nitrogen atmosphere until needed. To a clean, dry 50-L multi-necked RBF labeled as FLASK #2 (equipped with an agitator motor, agitator fitting, thermowell, thermocouple, condenser, and nitrogen bubbler), |
| 7.57 kg | of Resorcinol was charged, followed by |
| 26.1 L | of WFI water. Agitation was started. Nitrogen was bubbled through the solution or 43 minutes before charging |
| 4.5 kg | of 50% (w/w) Sodium Hydroxide, aqueous solution. |
| 4.3 g | of Copper (II) Sulfate Pentahydrate was then charged to FLASK #2. Nitrogen was bubbled through the solution for 43 minutes. The contents of FLASK #2 were then agitated at 20 ± 5° C. for 4 minutes until a complete solution was obtained. FLASK #2 was re-labeled as Step 1.34—FLASK#2—Resorcinol, WFI) aqueous solution, then held under a nitrogen atmosphere until needed. To a clean, dry 200-L reactor, the Resorcinol, (WFI) aqueous solution was charged through a polish filter. FLASK #2 was rinsed with |
| 11.2 L | of WFI water, and the rinse was charged to the reactor. The contents were agitated for 57 minutes, while nitrogen was bubbled through the solution, before being heated to 75 ± 5° C. The agitator speed was then set to ~280 rpm. While maintaining the temperature at 75 ± 5° C., the 2-bromo-5-hydroxybenzoic Salt (WFI) aqueous solution was charged at a rate of ~2.7 kg/15 minutes. FLASK #1 was rinsed with |
| 3.7 L | of WFI water. The rinse was charged to the reactor over 5 minutes while maintaining the temperature at 75 ± 5° C. The contents were then agitated at 75 ± 5° C. for 65 minutes. A representative IPC sample was withdrawn from the reactor and submitted to QC for HPLC analysis. The reaction was deemed incomplete, and was left to stir for additional time before a second IPC sample was submitted to QC. The reaction was then deemed complete. The reactor agitation was then set to ~300 rpm and the contents were slowly cooled to 20 ± 5° C. at a rate of ~5° C./30 minutes. The contents were agitated at 20 ± 5° C. for 1 hour 40 minutes before being filtered through a Nutsche filter. The reactor was rinsed with |
| 18.7 kg | of WFI water, and the rinse was used to wash the filter cake. The filter cake was then rinsed three more times with |
| 18.7 kg | of WFI water (each wash), followed by |
| 19.6 kg | of Glacial acetic acid. The filter cake was blown dry with nitrogen for 40 minutes. A representative sample was then withdrawn from the filter cake and submitted to QC for HPLC purity analysis. |
| | ~7.6 kg of wet, crude urolithin A or its di- or mono-Na-salt, were produced, which was carried forward to the next step. |

Step 2

Batch 1 of Urolithin A

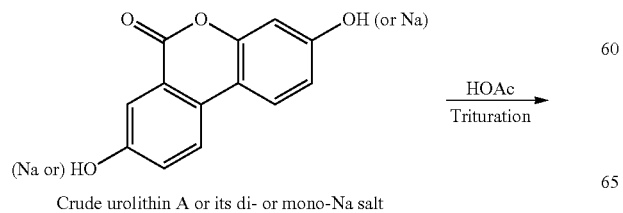

Crude urolithin A or its di- or mono-Na salt

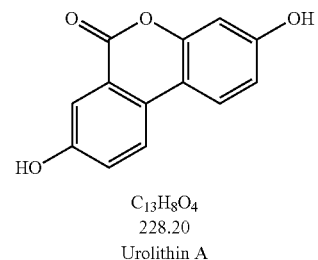

C$_{13}$H$_8$O$_4$
228.20
Urolithin A

Batch 3 of Urolithin A

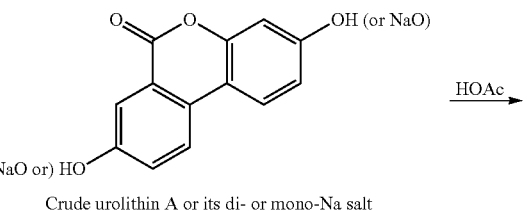

Crude urolithin A or its di- or mono-Na salt

| Reagents/Materials | MW | Eqs. | Moles | Density | Amt. |
|---|---|---|---|---|---|
| Urolithin A or its di- or mono-Na-salt | 228.20 | — | — | — | 5.15 kg |
| Glacial Acetic Acid, ≥99% | 60.05 | 19 vol | — | 1.049 | 55.6 kg |
| Water for Injection Quality (WFI) water | 18.02 | 19 vol | — | 1.00 | 53.0 kg |

To a clean, dry 200-L reactor equipped with a scrubber, 5.15 kg of urolithin A or its di- or mono-Na-salt was charged, followed by 55.6 kg of Glacial Acetic Acid. Agitation was set to ~320 rpm, and the contents were heated to reflux (115 ± 5° C.). The contents were agitated at reflux for 18 hours 28 minutes before cooling the reactor to 100 ± 5° C. The contents were agitated at 100 ± 5° C. for 7 hours 7 minutes. A glass-lined Nutsche filter was then pre-heated with steam before being used to filter the contents of the reactor. The reactor was rinsed twice with hot water (53.0 kg total of WFI water, pre-heated to 95 ± 5° C. in a 50-L RBF), and the filter cake was blown dry with nitrogen for 60 minutes. Two representative samples were then withdrawn from the filter cake. One sample was submitted to QC for HPLC analysis. The other sample was further dried by the Project Chemist before being submitted for residual Copper analysis (Cu = 1 ppm). The wet urolithin A was transferred to a vacuum oven and dried to constant weight at ≤55° C. Once at a constant weight, a representative sample was submitted to QC for HPLC analysis, as well as KF and HOAc content (KF = 0.20%; HOAc = 570 ppm). The dry urolithin A was screened and placed in a clean Curtek container for storage.

1.260 kg of urolithin A were produced.

-continued

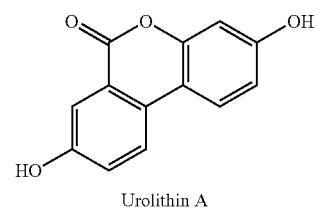

Urolithin A

Batch 2 of Urolithin A

| Reagents/Materials | MW | Eqs. | Moles | Density | Amt. |
|---|---|---|---|---|---|
| urolithin A or its di- or mono-Na-salt | 228.20 | — | — | — | 6.25 kg |
| Glacial Acetic Acid, ≥99% | 60.05 | 19 vol | — | 1.049 | 55.6 kg |
| Water for Injection Quality (WFI) water | 18.02 | 19 vol | — | 1.00 | 53.0 kg |

To a clean, dry 200-L reactor equipped with a scrubber, 6.25 kg of urolithin A or its di- or mono-Na-salt was charged, followed by 55.6 kg of Glacial Acetic Acid. Agitation was set to ~320 rpm, and the contents were heated to reflux (115 ± 5° C.). The contents were agitated at reflux for 18 hours 4 minutes before cooling the reactor to 100 ± 5° C. The contents were agitated at 100 ± 5° C. for 11 hours 13 minutes. A glass-lined Nutsche filter was then pre-heated with steam before being used to filter the contents of the reactor. The reactor was rinsed twice with hot water (53.0 kg total of WFI water, pre-heated to 95 ± 5° C. in a 50-L RBF), and the filter cake was blown dry with nitrogen for 1 hour. Two representative samples were then withdrawn from the filter cake. One sample was submitted to QC for HPLC analysis. The other sample was further dried by the Project Chemist before being submitted for residual Copper analysis (Cu = 1 ppm). The wet urolithin A was transferred to a vacuum oven and dried to constant weight at ≤55° C. Once at a constant weight, a representative sample was submitted to QC for HPLC analysis, as well as KF and HOAc content (KF = 0.31%; HOAc = 1140 ppm). The dry urolithin A was screened and placed in a clean Curtek container for storage.

1.250 kg of urolithin A were produced.

| Reagents/Materials | MW | Eqs. | Moles | Density | Amt. (kg) |
|---|---|---|---|---|---|
| Urolithin A or its di- or mono-Na-salt | 228.20 | — | — | — | 7.6 |
| Glacial Acetic Acid, ≥99% | 60.05 | 19 vol | — | 1.049 | 78.1 |
| Water for Injection Quality (WFI) water | 18.02 | 19 vol | — | 1.00 | 74.5 |

| | |
|---|---|
| | To a clean, dry 200-L reactor equipped with a scrubber, |
| 7.6 kg | of urolithin A di-Na-salt was charged, followed by |
| 78.1 kg | of Glacial Acetic Acid. Agitation was set to ~300 rpm, and the contents were agitated at 20 ± 5° C. for 18 hours 25 minutes. The contents were then filtered through a glass-lined Nutsche filter, using |
| 74.5 kg | of WFI water to rinse the reactor. The reactor rinse was used to wash the filter cake, which was then blown dry with nitrogen for 1 hour. Two representative samples were then withdrawn from the filter cake. One sample was submitted to QC for HPLC analysis. The other sample was further dried by the Project Chemist before being submitted for residual Copper analysis (Cu = 3 ppm). The wet urolithin A was transferred to a vacuum oven and dried to constant weight at ≤55° C. Once at a constant weight, a representative sample was submitted to QC for HPLC analysis, as well as KF and HOAc content (KF = 0.23%; HOAc = 0 ppm). The dry urolithin A was screened and placed in a clean Curtek container for storage. |
| | 2.075 kg of urolithin A were produced. |

Example 3—Scaled Up, 50 kg, GMP Synthesis of Urolithin A

| Reagents/Materials | Amount |
|---|---|
| 2-Bromo-5-hydroxybenzoic acid | 26.7 kg |
| 50% NaOH | 43.3 kg |
| Resorcinol | 54.2 kg |
| Copper (II) Sulfate Pentahydrate | 31 g |
| Glacial Acetic acid | 267 kg |
| Purified Water (PUW) | 914 kg |

Procedures:
1. Pre-weigh 54.2±0.2 kg of Resorcinol to solids charging bin 1 and solids charging bin 2.
2. Purge the headspace of solids charging bin 1 and solids charging bin 2 with LP $N_2$.
3. Pre-weigh 36.5±2.0 kg of PUW to mobile tank 1.
4. Perform three vacuum inerting cycles on reactor 1.
5. Transfer the PUW in mobile tank 1 to reactor 1.
6. Vacuum charge 32.5±0.5 kg of 50% NaOH to reactor 1.
7. Start agitation, and then purge nitrogen for a minimum of 15 min.
8. Transfer the Resorcinol in solids charging bin 1 and solids charging bin 2 to reactor 1.
9. Verify dissolution.
10. Transfer the content of reactor 1 to mobile tank 2.
11. Pre-weigh 14.0±2.0 kg of PUW to mobile tank 1.
12. Transfer the PUW in mobile tank 1 to reactor 1.
13. Transfer the rinse in reactor 1 to mobile tank 2.
14. Pre-weigh 26.7±0.2 kg of 2-Bromo-5-hydroxybenzoic acid to solids charging bin 3.
15. Purge the headspace of solids charging bin 3 with LP $N_2$.
16. Pre-weigh 48.8±2.0 kg of PUW to mobile tank 1.
17. Perform three vacuum inerting cycles on reactor 1.
18. Transfer the PUW in mobile tank 1 to reactor 1.
19. Vacuum charge 10.8±0.5 kg of 50% NaOH to reactor 1.
20. Start agitation, and then purge nitrogen for a minimum of 15 min.
21. Transfer the 2-Bromo-5-hydroxybenzoic acid in solids charging bin 3 to reactor 2.
22. Start agitation, and then verify dissolution.
23. Slowly transfer the content of reactor 2 to reactor 3 via a 0.6 micron polish filter while maintaining a temperature of 75±5° C. in reactor 3. Note: This addition may take approx. 4 hours or more.
24. Pre-weigh 14.0±2.0 kg of PUW to mobile tank 1.
25. Transfer the PUW in mobile tank 1 to reactor 2.
26. Transfer the rinse in reactor 2 to reactor 3 via a 0.6 micron polish filter.
27. Pre-weigh 31±2.0 g of copper (II) sulfate pentahydrate to a 1 liter sample jar.
28. Transfer the copper (II) sulfate pentahydrate in the sample jar to reactor 3.
29. Perform three vacuum inerting cycles on reactor 3.
30. Receive the Resorcinol solution and rinse from mobile tank 2 (reactor 1 items 10 and 13) via a 0.6 micron polish filter.
31. Start agitation, and then purge nitrogen for a minimum of 15 min.
32. Adjust the batch temperature to 75±5° C.
33. Receive the 2-Bromo-5-hydroxybenzoic acid solution and rinse from reactor 2 (reactor 2 items 23 and 26) while maintaining a temperature of 75±5° C. Note: This addition may take approx. 4 hours or more.
34. Hold the content of reactor 3 at 75±5° C. for a minimum of 2 hours.
35. Obtain an IPC sample via the dip tube sampler.
36. Once sample passes criteria, cool the batch temperature of reactor 3 at 20±5° C.
37. Hold the content of reactor 3 at 20±5° C. for a minimum of 1 hour.
38. Transfer half of the slurry in reactor 3 to mobile basket filter receiving the mother liquors in mobile tank 3.
39. Pre-weigh 267±5 kg of PUW to mobile tank 1.
40. Transfer the PUW in mobile tank 1 to mobile basket filter receiving the mother liquors in mobile tank 3.
41. Repeat items 38 to 40. NOTE: The second PUW wash may be put through reactor 3 as a rinse in three portions.
42. Obtain a FIO wet cake sample for purity.
43. Transfer the wet cake from mobile basket filter to reactor 3 via the main way.
44. Perform three vacuum inerting cycles using $N_2$.
45. Vacuum charge 267±2 kg of glacial acetic acid to reactor 3 and 0.6 micron polish filter.
46. Heat the content of reactor 3 to 115±5° C., and hold for approx. 18 hours or more.

47. Cool the batch temperature of reactor 3 to 20±5° C.
48. Transfer half of the slurry in reactor 3 to centrifuge receiving the mother liquors in mobile tank 3.
49. Pre-weigh 267±5 kg of PUW to mobile tank 1.
50. Transfer approximately half of the PUW in mobile tank 1 to centrifuge receiving the mother liquors in mobile tank 3.
51. Transfer the remaining amount of the slurry in reactor 3 to centrifuge receiving the mother liquors in mobile tank 3.
52. Transfer the remaining amount of PUW in mobile tank 1 to reactor 3 in a number of portions (e.g., three portions).
53. Transfer the rinse in reactor 3 to centrifuge receiving the mother liquors in mobile tank 3.
54. Transfer the wet cake in centrifuge to solids bulk container.

Conical Screw Dryer

55. Transfer the wet cake in solids bulk container to conical screw dryer.
56. Dry in conical screw dryer under full vacuum at 55° C. on the jacket.
57. Sample conical screw dryer for acetic acid content, water content and purity.
58. Transfer the conical screw dryer to HDPE drums lined with a polyethylene bag using a continuous bag liner.
59. Obtain release sample.
60. QC testing (e.g., USP <61> and <62>).

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method of preparing a salt of urolithin A, comprising: combining in an alkaline aqueous solution a copper-containing catalyst, 2-bromo-5-hydroxybenzoic acid, and resorcinol, thereby forming the salt of urolithin A; wherein the amount of the copper-containing catalyst is at least a trace amount but no more than 0.01 molar equivalents relative to the amount of 2-bromo-5-hydroxybenzoic acid; and the molar ratio of resorcinol to 2-bromo-5-hydroxybenzoic acid is about 3.5:1 to about 5:1.

2. The method of claim 1, wherein the copper-containing catalyst is selected from the group consisting of copper powder, copper-bronze couple, $CuSO_4$ pentahydrate, $CuSO_4$ hydrate, anhydrous $CuSO_4$, $Cu(acac)_2$, CuCl, $CuCl_2$, CuBr, $CuBr_2$, CuI, $Cu_2O$, CuO, CuOTf, CuCN, and mixtures thereof.

3. The method of claim 1, wherein the alkaline aqueous solution comprises LiOH, NaOH, KOH, CsOH, $Na_2CO_3$, $CaCO_3$, or $Cs_2CO_3$.

4. The method of claim 1, wherein the alkaline aqueous solution comprises LiOH, NaOH, KOH, CsOH, $Na_2CO_3$, $CaCO_3$, or $Cs_2CO_3$; and the molar ratio of LiOH, NaOH, KOH, CsOH, $Na_2CO_3$, $CaCO_3$, or $Cs_2CO_3$ to 2-bromo-5-hydroxybenzoic acid is about 2.8:1 to about 5:1.

5. The method of claim 1, wherein the molar yield of the salt of urolithin A is at least about 40% relative to the amount of 2-bromo-5-hydroxybenzoic acid.

6. The method of claim 1, wherein the salt of urolithin A is urolithin A monosodium salt.

7. The method of claim 1, wherein the salt of urolithin A is urolithin A disodium salt.

8. The method of claim 1, wherein the alkaline aqueous solution is heated at a temperature in the range of about 60° C. to about 90° C.

9. The method of claim 1, further comprising isolating the salt of urolithin A, to give an isolated salt of urolithin A.

10. The method of claim 9, wherein the isolated salt of urolithin A is isolated by filtration.

11. The method of claim 9, wherein the isolated salt of urolithin A contains less than about 1 ppm copper.

12. The method of claim 9, further comprising combining a Bronsted acid and the isolated salt of urolithin A, to give a slurry.

13. The method of claim 12, wherein the Bronsted acid is a carboxylic acid.

14. The method of claim 13, wherein the carboxylic acid is acetic acid.

15. The method of claim 13, wherein the carboxylic acid is glacial acetic acid.

16. The method of claim 9, wherein the isolated salt of urolithin A is urolithin A monosodium salt.

17. The method of claim 9, wherein the isolated salt of urolithin A is urolithin A disodium salt.

18. The method of claim 9, wherein the isolated salt of urolithin is at least 95% pure.

19. The method of claim 12, wherein the slurry is heated at a temperature in the range of about 100° C. to about 130° C.

20. The method of claim 12, wherein the slurry is maintained at a temperature in the range of about 10° C. to about 30° C.

21. The method of claim 12, further comprising isolating urolithin A from the slurry.

22. The method of claim 21, wherein the urolithin A is isolated by filtration.

23. The method of claim 21, wherein the isolated urolithin A is at least 99% pure.

* * * * *